(12) United States Patent
Hawman et al.

(10) Patent No.: US 9,622,714 B2
(45) Date of Patent: Apr. 18, 2017

(54) SYSTEM AND METHOD FOR PHOTOGRAPHIC DETERMINATION OF MULTICHANNEL COLLIMATOR CHANNEL POINTING DIRECTIONS

(75) Inventors: Eric G. Hawman, Schaumburg, IL (US); Robert Kasper, Chicago, IL (US)

(73) Assignee: Siemens Medical Solutions USA, Inc., Malvern, PA (US)

( * ) Notice: Subject to any disclaimer, the term of this patent is extended or adjusted under 35 U.S.C. 154(b) by 813 days.

(21) Appl. No.: 13/155,430

(22) Filed: Jun. 8, 2011

(65) Prior Publication Data
US 2012/0314062 A1  Dec. 13, 2012

(51) Int. Cl.
| | | |
|---|---|---|
| *G06K 9/00* | (2006.01) | |
| *A61B 6/03* | (2006.01) | |
| *G06T 11/00* | (2006.01) | |
| *A61B 6/06* | (2006.01) | |
| *G06T 7/00* | (2017.01) | |

(52) U.S. Cl.
CPC ............. *A61B 6/037* (2013.01); *A61B 6/06* (2013.01); *G06T 7/0018* (2013.01); *G06T 11/005* (2013.01); *G06T 2207/10108* (2013.01)

(58) Field of Classification Search
CPC ........ G06T 11/005; G06T 2207/10108; G06T 7/0018; A61B 6/037; A61B 6/06
USPC .................................................. 348/135, 142
See application file for complete search history.

(56) References Cited

U.S. PATENT DOCUMENTS

| | | | |
|---|---|---|---|
| 5,825,842 A | 10/1998 | Taguchi | |
| 6,175,615 B1 * | 1/2001 | Guru et al. | 378/149 |
| 6,580,939 B1 * | 6/2003 | Chaney et al. | 600/425 |
| 6,646,730 B2 * | 11/2003 | Hwang et al. | 356/124 |
| 7,635,847 B2 * | 12/2009 | DiFilippo | 250/363.09 |
| 7,819,320 B2 | 10/2010 | Modavis et al. | |
| 2005/0084072 A1 * | 4/2005 | Pinchot | 378/154 |
| 2007/0069136 A1 * | 3/2007 | Hawman | 250/363.1 |
| 2007/0268997 A1 | 11/2007 | Zhu et al. | |
| 2010/0102239 A1 * | 4/2010 | Hahn et al. | 250/363.05 |
| 2011/0096895 A1 * | 4/2011 | Kurochi | 378/19 |
| 2012/0165656 A1 * | 6/2012 | Montag et al. | 600/424 |

* cited by examiner

*Primary Examiner* — Zhihan Zhou (57) ABSTRACT

A system and method are disclosed for obtaining pointing directions for every channel of a collimator which can then be used during the image reconstruction process to more accurately estimate the direction from which radiation has been received. The disclosed system and method provide for photographic measurement and analysis of individual collimator channel to determine the pointing directions for every channel in the collimator. This information is obtained by photographing the front and back sides of the collimator, and analyzing the digital image data to obtain the pointing angle of each channel. The resulting information, referred to as a "vector map" is included in the firmware of the collimator so that it can be called on during the projection and back-projection steps of the algorithm.

18 Claims, 12 Drawing Sheets

SYSTEM AND METHOD FOR PHOTOGRAPHIC DETERMINATION OF MULTICHANNEL COLLIMATOR CHANNEL POINTING DIRECTIONS

FIELD OF THE DISCLOSURE

The disclosure is related in general to systems and methods used in nuclear imaging, and more particularly to systems and methods for characterizing exact collimator channel pointing directions for use in SPECT image reconstruction to improve image quality; i.e. to reduce artifacts, and distortions, to improve image contrast and spatial resolution.

BACKGROUND

Collimators are frequently used in radiation imagers to ensure that only radiation beams passing along a direct path from the known radiation source strike the detector thereby minimizing detection of beams of scattered or secondary radiation. Particularly in radiation imagers used for medical diagnostic analysis or for non-destructive evaluation procedures, it is important that only radiation emanating from a known source and passing along a direct path from that source be detected and processed by the imaging equipment. If the detector is struck by undesired radiation such as that passing along non-direct paths to the detector, performance of the imaging system can be compromised.

One diagnostic technology that incorporates collimators is the gamma camera typically utilized in Single Photon Emission Computed Tomography (SPECT) scanning, which is a nuclear medicine procedure in which gamma camera(s) have traditionally rotated around the patient taking pictures from many angles. From these images, a computer is employed to form a tomographic (cross-sectional) image of the internal area-of-interest within the patient using a calculation process that is similar to that used in X-ray Computed Tomography (CT) and in Positron Emission computed Tomography (PET).

In the instance of SPECT scanning, a subject (patient) is infused with a radioactive substance that emits gamma rays. Conventionally, a gamma camera includes a transducer to receive the gamma rays and record an image therefrom. In order for the image to be a true representation of the subject being studied, a collimator having collimating apertures (referred to as channels) is positioned between the transducer and the subject to screen out all of the gamma rays except those directed along a straight line through the collimator channels between a particular part of the subject and a corresponding particular part of the transducer. Traditionally, the collimator is made of a radiation opaque material such as lead, and collimating channels have been formed therein by various means such as drilling, casting, or lamination of corrugated strips of lead foil.

Owing to limitations in current manufacturing techniques, collimating channels have angular pointing errors. These errors cause distortions in the resulting nuclear medicine images, particularly those of Single Photon Emission Computed Tomography (SPECT) systems. Thus, it would be desirable to have a system and method that can provide correction for such angular pointing errors in the collimator channels in order to reduce image distortions and improve nuclear medicine image resolution.

SUMMARY

This disclosed system and method enable efficient, fast, and accurate determination of collimator pointing characteristics. The result is a list of positions and pointing directions for every channel ("hole") of the collimator which can then be used during the image reconstruction process to more accurately estimate the direction from which radiation has been received. This, in turn, can minimize artifacts and provide a more accurate reconstructed image of patient tissue.

The disclosed system and method provide for photographic measurement and analysis of individual collimator channels to determine the positions, pointing directions, and entrance and exit channel geometry, for every channel in the collimator. This information is obtained by photographing the front and back of the collimator, and analyzing the digital image data to obtain the pointing angle of each channel. The resulting information, referred to as a "vector map" is included in the firmware of the collimator so that it can be called on during the projection and back-projection steps of the SPECT image reconstruction algorithm.

According to an embodiment, a method for obtaining a map of channel orientations, i.e. a vector map, of a multichannel collimator for a nuclear medicine imaging system is based on high-resolution digital photography. The multichannel collimator has both a first side and a second side and a plurality of channels extending there through, where each of the plurality of channels has openings at the first side and the second side of the collimator. First, a digital image of the first side of the collimator is generated and the positions of each channel openings are determined by digital image analysis. Similarly, by analysis of a digital image of the second side of the collimator, the positions of the channel openings on the second side of the collimator are obtained. From the relative positions of each channel opening between the first side and the second side of the collimator an orientation vector for each of the plurality of channels is calculated.

The disclosed system and method utilize digital photographic techniques to produce digital images of the collimator, and process this digital image data to derive collimator hole characteristics. With the recent introduction in the nuclear medicine market of fast scanning for nuclear cardiology, the development of multifocal converging collimation has gained renewed commercial interest for the realization of faster cardiac SPECT study acquisition. The disclosed system and method will provide improved reconstructed images of higher quality (i.e. less distortion and improved spatial resolution).

BRIEF DESCRIPTION OF THE DRAWINGS

The accompanying drawings illustrate preferred embodiments of the disclosure so far devised for the practical application of the principles thereof, and in which.

All drawing figures are schematic and the structures shown are not to scale and are not intended to show actual dimensions.

DETAILED DESCRIPTION

Figure 1:
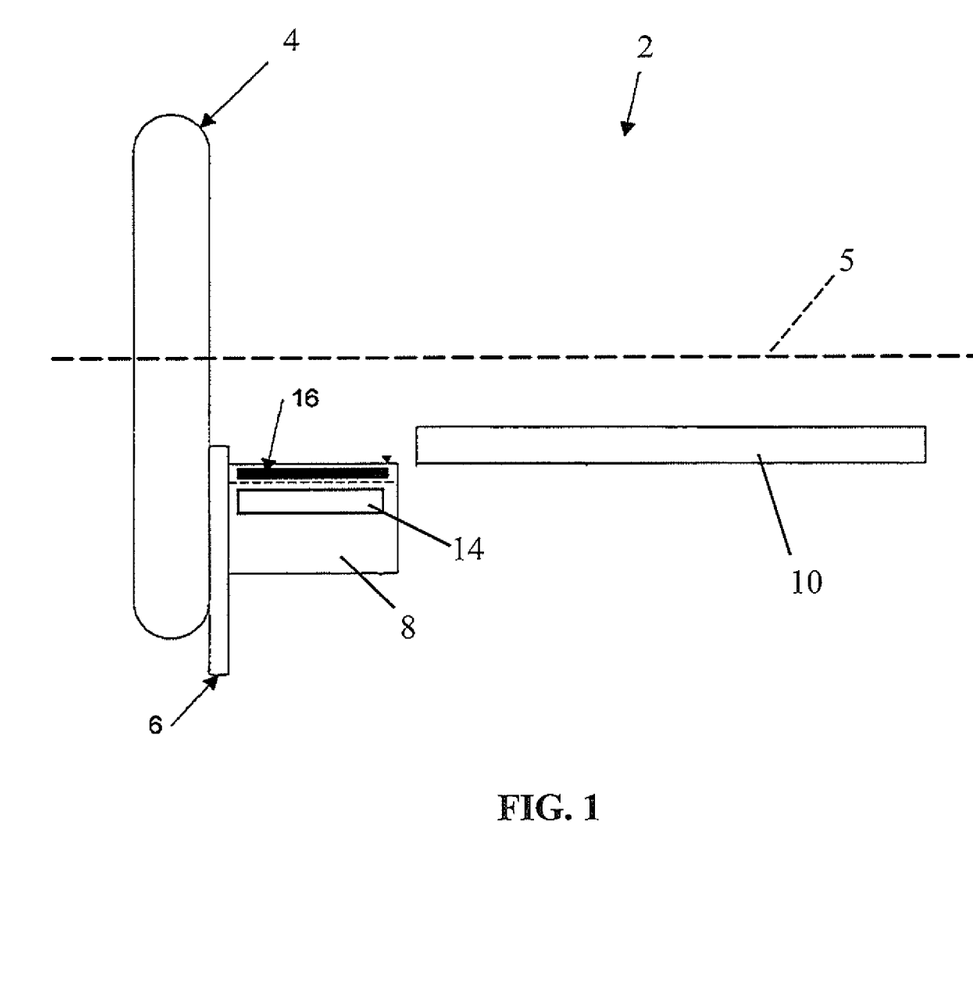
FIG. 1 is a schematic side view of a nuclear medicine imaging system.

FIG. 1 shows a schematic illustration of a nuclear medicine imaging system 2 that includes a patient handling system 10 and a gamma camera detector head 8. The detector head 8 is generally mounted on an arrangement formed by a rail 6 and a gantry 4 that enables positioning the detector head 8 relative to the patient on the patient handling system 10. The detector head 8 comprises a scintillation crystal 14 and a removable multichannel collimator 16. The collimator 16 is positioned such that it is between the gamma ray source in the patient and the scintillation crystal 14 during the operation of the nuclear medicine imaging system 2. The gantry 4 is capable of rotating the detector head 8 around the center line 5 of the gantry 4, and the rail 6 allows the detector head 8 to be moved toward and away from the center line of gantry 4. Some systems can be configured with more than one detector head 8. The method of the present disclosure is concerned with the collimation of the gamma rays traveling from the radiation source in the patient to the scintillation crystal 14.

Figure 2:
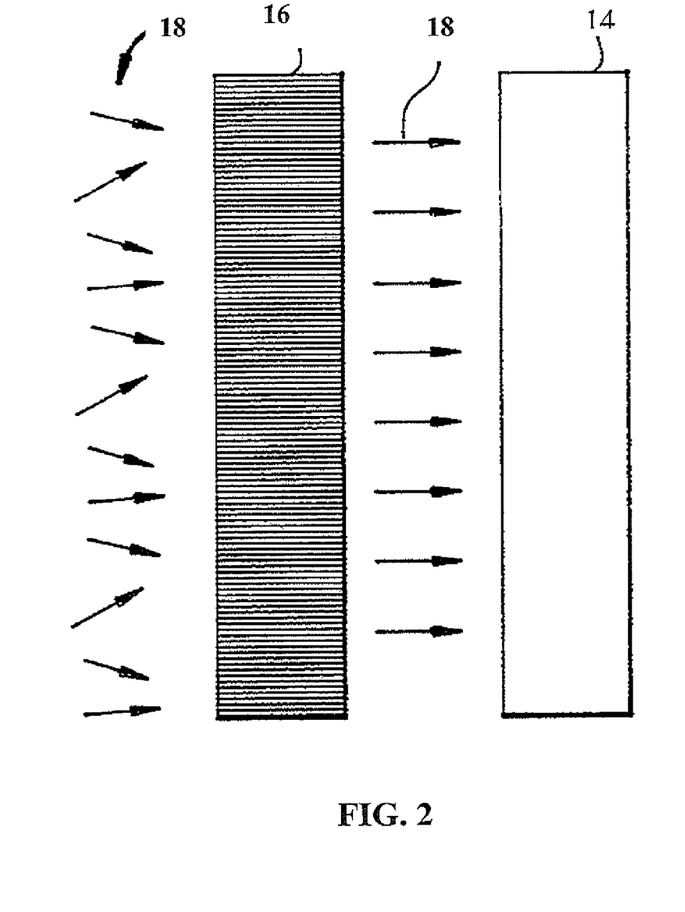
FIG. 2 is a schematic detailed illustration of a multichannel collimator and a scintillation crystal of a gamma ray detector head.

FIG. 2 is a more detailed view of the collimator 16 and the scintillation crystal 14. The collimator 16 collimates the gamma radiation generally indicated by reference numeral 18a before the radiation 18a reaches the scintillation crystal 14. An ideal collimator 16 blocks all off-axis rays, so that only on-axis radiation beams 18b reaches the detector surface. The on-axis radiation beams 18b propagate in the direction intended by the collimator channels, which in this example are perpendicular to the surface of the collimator 16 and are parallel. In FIG. 2, the collimator 16 is a parallel-channel, non-focusing collimator, but this is only for convenience and the disclosed system and method apply equally well with astigmatic collimators and focusing collimators such as fan-beam collimators and cone-beam collimators.

Figure 3:
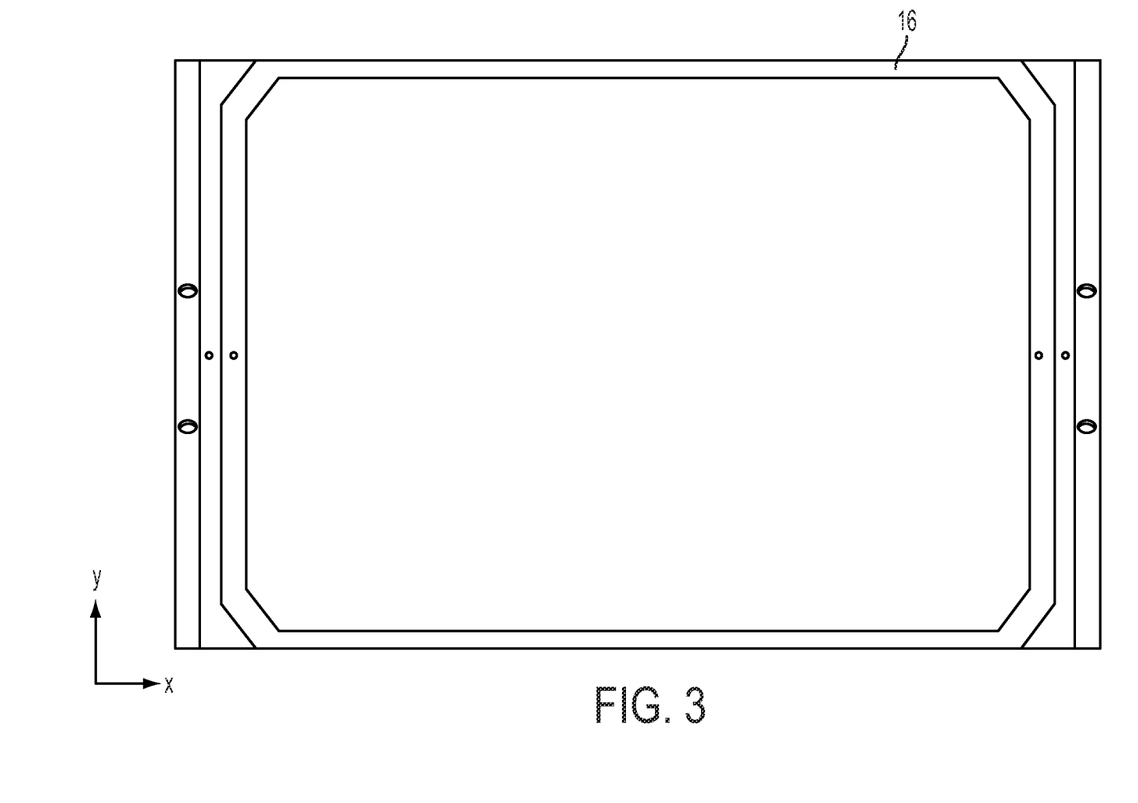
FIG. 3 is a photograph of a multichannel collimator for use in the system of FIG. 1.
Figure 4:
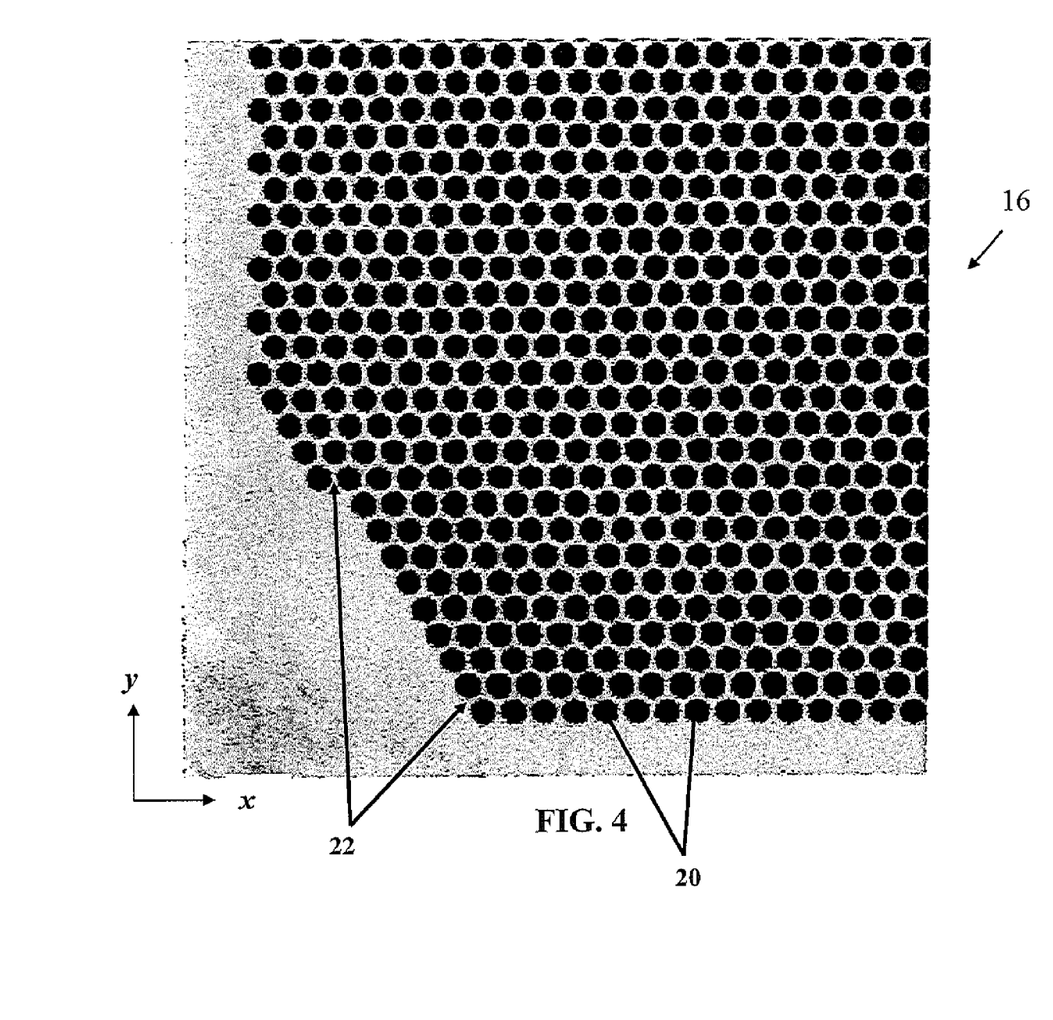
FIG. 4 is a closeup image of the lower left corner of the multichannel collimator of FIG. 3.

FIG. 3 is a photograph of one side of the collimator 16. FIG. 4 is a magnified detailed view of the lower left corner of the collimator 16 of FIG. 3. The illustrated collimator has been manufactured by casting lead, and it includes 47,648 individual collimating channels 20, each of which is approximately 1.9 millimeters in diameter. The septal 22 between the collimating channels 20 varies in thickness from 0.2 to 0.4 mm.

The disclosed system and method provide an efficient and accurate method of measuring collimator's actual channel pointing directions that is compiled into a distortion correction "vector map" for any given collimator. Thus, when a collimator is installed in a SPECT system, for example, the corresponding vector map for that particular collimator would be made available to the SPECT system, e.g. by loading the vector map data into the SPECT system's controller/computer so that the vector map data can be incorporated into the SPECT reconstruction. According to an embodiment, the vector map comprises a two dimensional map in which each vector indicates the orientation of the individual collimator channels 20 and thus represents the direction from which the collimated radiation beams 18b are received by the scintillation crystal 14 through each of the collimator channels 20. Thus, for the exemplary collimator 16 of FIG. 3, the vector map would include 47,648 individual vectors.

Figure 5:
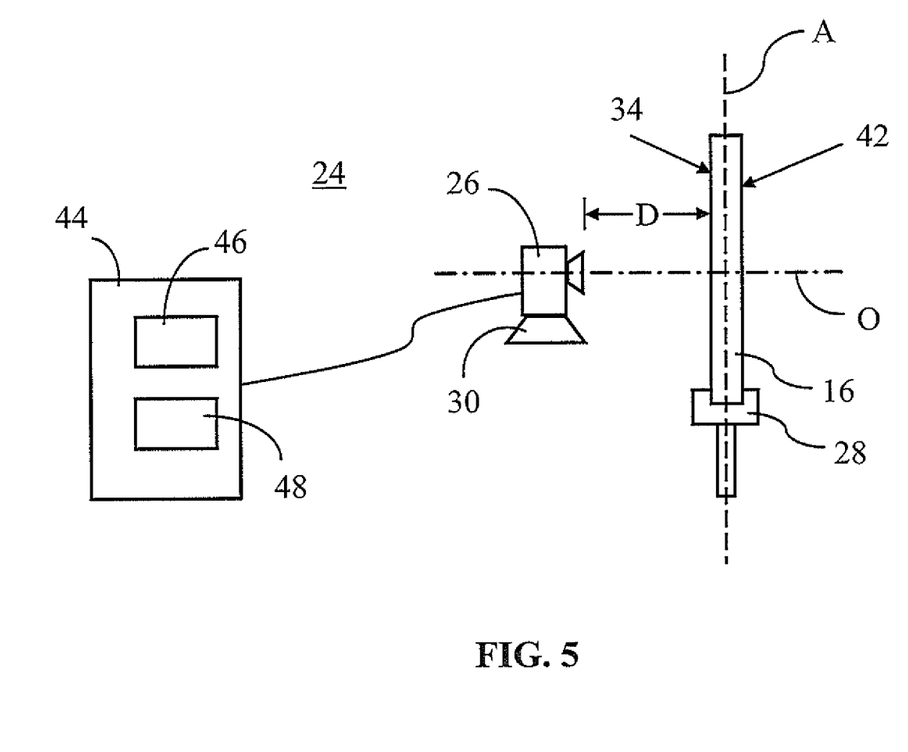
FIG. 5 is a schematic illustration of a calibration system for characterizing a collimator according to an embodiment.

Referring to FIG. 5, a calibration system 24 for generating a vector map of a collimator 16 is illustrated. In this embodiment, the calibration system 24 includes a high resolution digital camera 26 mounted on a camera mount 30 and a rotatable fixture 28 for holding the collimator 16. The camera 26 is chosen to provide images with spatial resolution adequate for the determination of the positions of the collimator's collimator holes 20. This implies that the spatial resolution of the camera 26 should clearly define the septa 22 between the collimator holes 20. This is achieved when the pixel size and spatial resolution of the image produced by the camera 26 is approximately one-half the width of the septa 22 or smaller. It is also desirable for the efficiency of the overall procedure that the field-of-view of the camera 26 be large enough to capture each face of the collimator with a single exposure.

Throughout this document, the term "photographing" refers to taking or acquiring a digital image of a subject using the digital camera 26. The output of this photographing with the digital camera 26 is a digital image data. The digital camera 26 is generally an electronic imager using a CCD or a CMOS chip.

The calibration system 24 also includes a controller 44 (e.g. a computer) that is configured with a processor 46 suitable for performing image processing necessary to process the digital image data generated by the camera 26. The controller 44 is also provided with a data storage unit 48 suitable for storing the digital image data. The data storage unit 48 can be one or more of data storage devices commonly used in computers.

Figure 6:
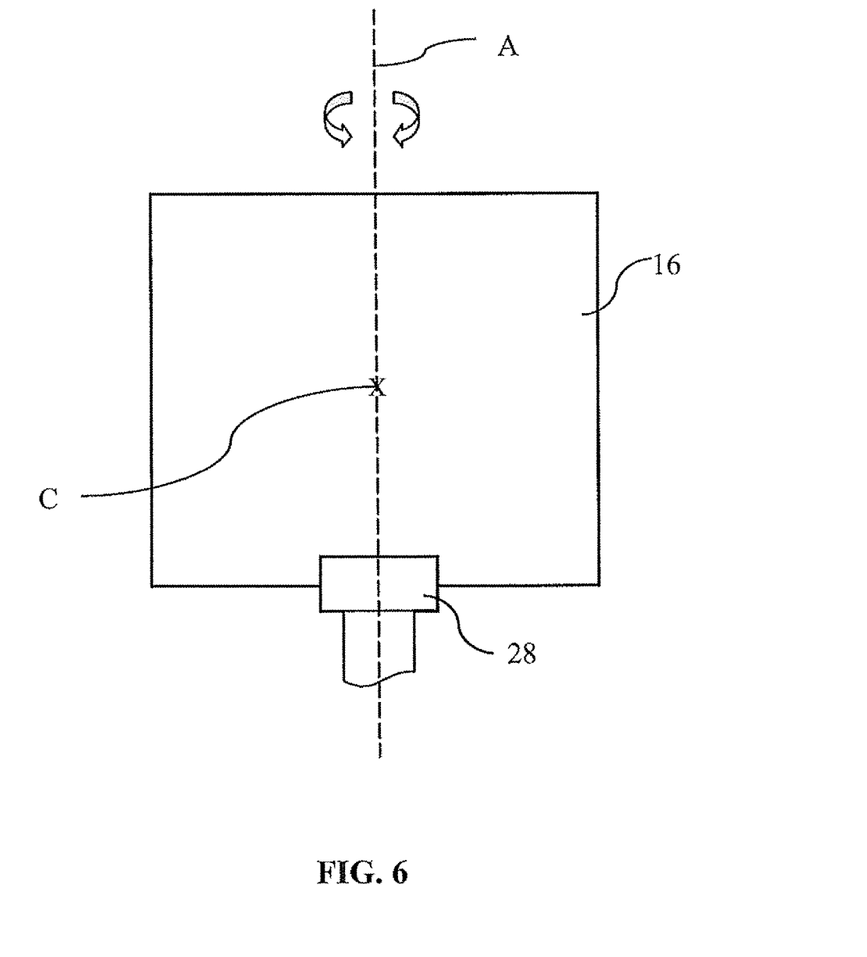
FIG. 6 is a schematic illustration of a multichannel collimator mounted on a fixture in the calibration system of FIG. 5.

The fixture 28 holds the collimator 16 in vertical orientation and the camera mount 30 is provided at a fixed position relative to the fixture 28 such that the camera 26 is at a fixed distance D from the surface of the collimator 16 mounted in the fixture 28. The collimator 16 has two sides 34 and 42. As shown in FIGS. 5 and 6, the fixture 28 is rotatable about its vertical axis A so that each of the two sides 34, 42 of the collimator 16 can be presented to the camera 26 for acquiring digital images of the two sides. The vertical axis A will also be referred to herein as the axis of rotation A.

Because the fixture 28 is configured to hold the collimator 16 in vertical orientation and have the vertical axis A of the fixture extend through the center of the thickness of the collimator 16. This configuration allows the two sides 34, 42 of the collimator 16 to be parallel to the vertical axis A of the fixture 28 and maintain the distance D from the camera 26 when each of the two sides 34, 42 are facing the camera 26. Ideally, the optical axis O of the camera would be exactly perpendicular to the vertical axis A of the fixture 28. This ensures that the optical axis of the camera to be perpendicular to the surfaces of the two sides 34, 42 of the collimator when facing the camera 26. Ideally, the optical axis of the camera 26 would also intersect the collimator surface at the mechanical center C of the collimator 16 so that the collimator is centered in the camera's field-of-view. When a given side of the collimator 16 is facing the camera 26, the spatial relationship between the camera 26 and the collimator 16 is characterized by the configuration described above. Ideally, the configuration of the camera 26 and the collimator 16 ensures there is no component of geometric distortion in the digital images of the two sides 34, 42 acquired by the camera 26 attributable to non-ideal alignment of the camera with respect to the surface of the collimator 16.

In order to generate the vector map for the collimator 16, the collimator 16 is mounted in the fixture 28 and oriented with one of the two sides 34, 42 of the collimator facing the camera 26 for acquiring a digital image of that side. It is not important which of the two sides is selected first but for this description of an exemplary embodiment, we will assume that the side 34 is selected as the first side facing the camera 26. The camera 26 is used to photograph a digital image of the first side 34 of the collimator. The resulting digital image is stored in the data storage unit 48 as a first image data which represents the positions of each channel openings on the first side 34 of the collimator 16. Next, the fixture 28 is rotated about its axis of rotation A 180 degrees so that the second side 42 of the collimator 16 is now facing the camera 26 and the second side 42 is photographed. The resulting digital image of the second side 42 is stored in the data storage unit 48 as a second image data which represents the positions of each channel openings on the second side 42 of the collimator 16. During the rotation of the collimator 16, the camera 26 is immobile so that the camera's position remains fixed relative to the fixture 28.

The term "channel opening" as used herein refers to the opening formed on the surface of the collimator 16 by the intersection of a given channel 20 and the surface of the collimator 16. Thus, for any given channel 20, there are two channel openings, one on the first side 34 and another on the second side 42 of the collimator 16. Thus, by comparing the positions of the two channel openings associated with a given channel 20 relative to one another using the first and second image data stored in the data storage unit 48, the orientation (i.e. the channel's vector) of the channel 20 can be determined.

Figure 7A:
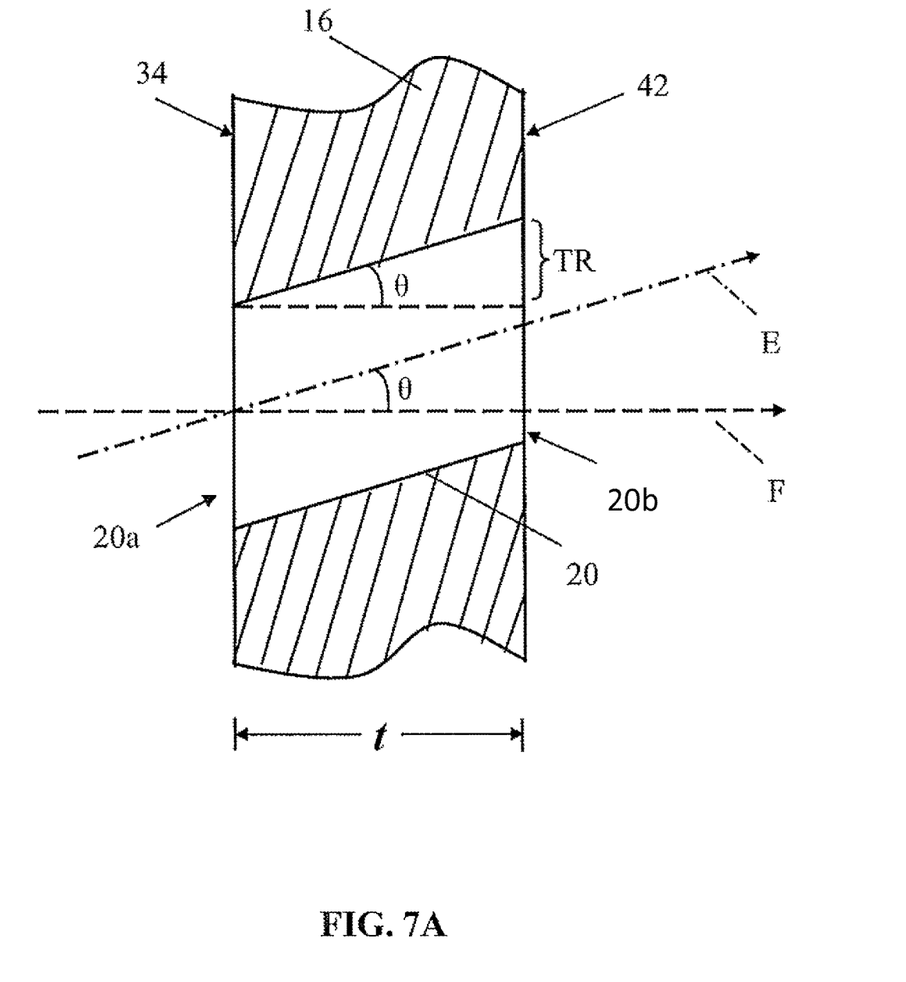
FIG. 7A is a schematic illustration of a cross-sectional view of one collimator channel.

The determination of the collimator channel's vector will be described in conjunction with the illustrations shown in FIGS. 7A and 7B. FIG. 7A shows a cross-sectional view of a collimator channel 20 of the collimator 16 taken through a plane along the y-axis according to the x-y reference axes shown in FIGS. 3 and 4. The collimator 16 has a known thickness t and the channel 20 extends through the thickness of the collimator 16 from the first side 34 to the second side 42. The channel opening on the first side 34 of the collimator is marked as 20a and the channel opening on the second side 42 of the collimator is marked as 20b. The orientation vector of the channel 20 is represented by the arrow E which is also the channel's longitudinal axis. The arrow F is perpendicular to the two surfaces 34, 42 of the collimator and extends through the center of the channel opening 20a. Thus, the arrow F represents the hypothetical orientation vector of the channel 20 if the channel were oriented orthogonally through the collimator. In the illustrated example, however, the two channel openings 20a, 20b are translated in the y-axis direction by amount TR.

Figure 7B:
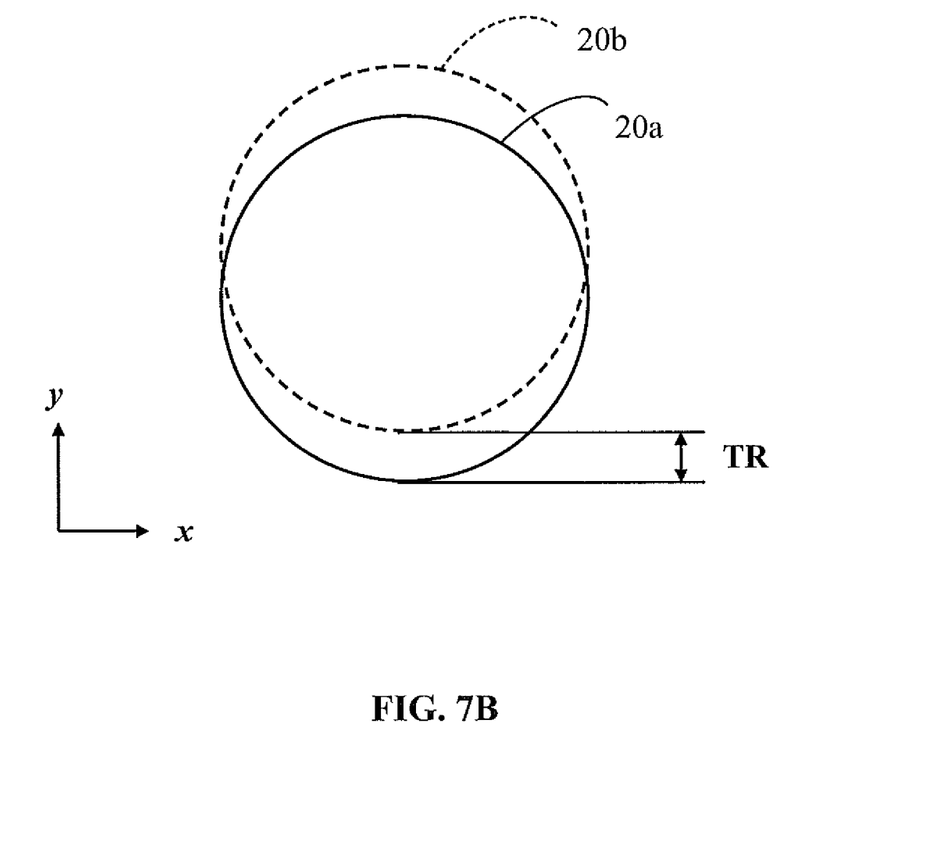
FIG. 7B is a schematic illustration of the image of a collimator channel, which shows the channel opening of the first side overlaid with the channel opening of the second side.

Referring to FIG. 7B, the first image data stored in the data storage unit 48 contains the digital image data representing, among others, the position of the channel opening 20a shown. The second image data stored in the data storage unit 48 contains the digital image data representing, among others, the position of the channel opening 20b shown in broken lines. By comparing the two image data, the translation TR can be determined. Since the thickness t of the collimator is known, once the translation TR is determined, the angular deviation θ of the channel 20 in the y-axis direction can be determined using the equation: $\tan(\theta) = TR/t$. The example shown is for determining the y-axis translation of the channel openings. A similar determination is made in the x-axis direction to determine the angular deviation in the x-axis direction.

The angular deviations in the x and y axes are the x-axis and y-axis components of the channel's orientation vector and, thus, the channel's orientation vector can be calculated. Such calculation would be carried out by the processor 46 of the calibration system 24 shown in FIG. 5. The processor 46 would perform this vector calculation for all of the channels 20 in the collimator 16 and generate a two-dimensional array of the vectors as the vector map for the collimator 16. The vector map information is thereafter used during the image reconstruction process (forward projection and back projection) in a nuclear medicine imaging system such as a SPECT in which the collimator 16 is installed.

In the above example, if the channel 20 were oriented orthogonally along the arrow F, the channel openings 20a and 20b would overlap one another without any relative translation (i.e. TR=0) and the orientation vector for that channel would be determined to be orthogonal to the first and second surfaces of collimator 16.

In order to compare the first image data to the second image data as discussed above, the relative positions of the collimator images must be known. This is because the images of the first and second sides 34, 42 of the collimator will be "flipped" left to right with respect to each other, such that the left-most holes in the image of the first side 34 will be the right-most-holes in the image of the second side 42. This is because the two digital images are taken by rotating the collimator 16 along the rotational axis A of the fixture 28 as shown in FIG. 5 and FIG. 6. Thus, one of the two image data must be flipped about the rotational axis A.

Ideally, the rotational axis A of the rotatable fixture 28 would be perfectly vertical and perfectly centered with respect to the intersection of the optical axis O, FIG. 5, on the collimator 16 so that simply flipping one of the two collimator image data about its vertical center would be sufficient. However, in reality, the rotational axis A of the fixture 28 is not perfectly vertical nor perfectly aligned with the centerline of the collimator 16 while the collimator 16 is rotated to face the camera 26. As a result, the image of the first side 34 of the collimator and, thus, the position of the collimator channel 20 on the first side 34, may be laterally translated with respect to the position of the corresponding collimator channels 20 on the second side 42. Such translation, if not corrected, can introduce errors in the calculation of the orientation vectors for the collimator's vector map. This undesired translation relating to the rotational axis A will be referred to herein as the "rotational error" of the fixture 28.

Figure 8:
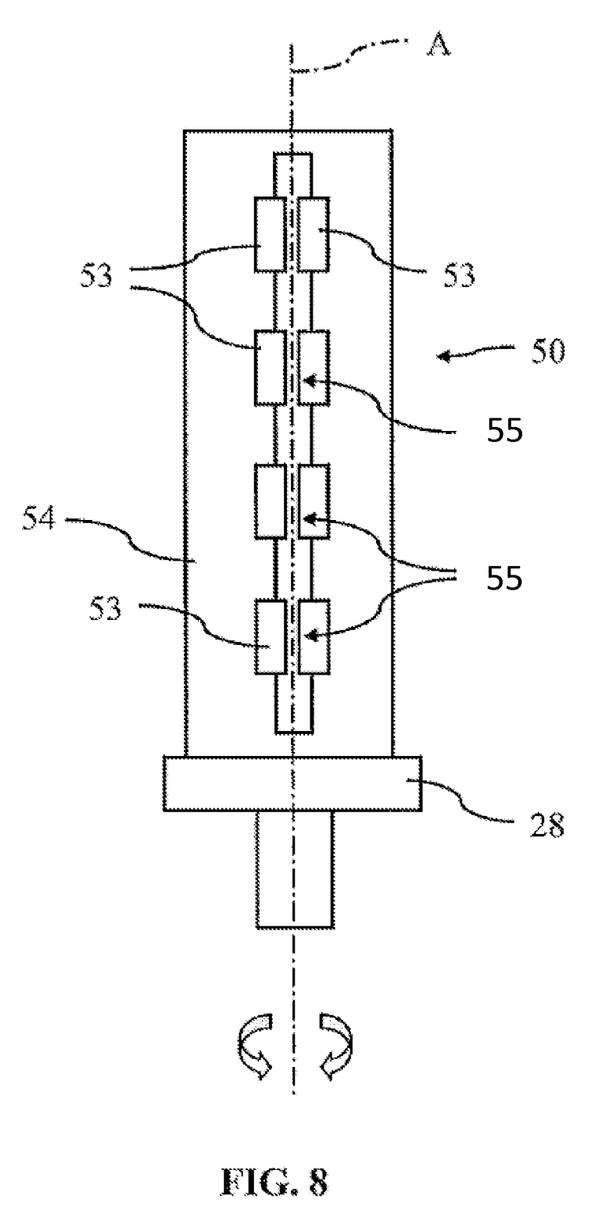
FIG. 8 is a schematic illustration of a rotational axis registration plate used in the method of the present disclosures.

According to an embodiment of the present disclosure, an appropriate correction for the rotational error can be obtained by determining the precise position of the rotational axis A of the fixture 28, the true rotational axis, in the x-y axes reference plane and performing the flipping of the first or second image data of the collimator 16 about the true rotational axis A. The position of the true rotational axis A can be obtained using a rotational axis registration plate 50 shown in FIG. 8. According to a preferred embodiment, the position of the true rotational axis A is determined to within ±10 μm. The inventors were able to experimentally confirm this using a prototype configuration which constitutes the embodiment described herein. Furthermore, the angle of rotation axis A, deviation from vertical in the x-y coordinates, see FIG. 3, can be determined to an accuracy of about ±0.001 degrees.

The rotational axis registration plate 50 comprises a plurality of slits 55 formed by multiple pairs of straight edges in parallel arrangement. The rotational axis registration plate 50 has two sides 52, 54 and the slits 55 are visible from both sides. In the illustrated example, the plurality of slits 55 are formed by pairs of razor blades 53 mounted on a frame with the straight edges of their blades facing each other in parallel configuration to form the plurality of slits 55. The straight edges of the razor blades are ideal for this purpose because straight edges do not have noticeable thickness. In order to determine the position of the true rotational axis A of the rotatable fixture 28, the rotational axis registration plate 50 is mounted on the fixture 28 in the orientation shown in FIG. 8 so that the plurality of slits 55 are in vertical orientation. However, the slits 55 do not have to be aligned with the rotational axis A of the fixture 28. The spatial relationship between the camera 26 and the fixture 28 is fixed and therefore that spatial relationship between the camera 26 and the rotational axis A of the fixture 28 is also fixed, because the rotation axis A is a property of the fixture.

Figure 9:
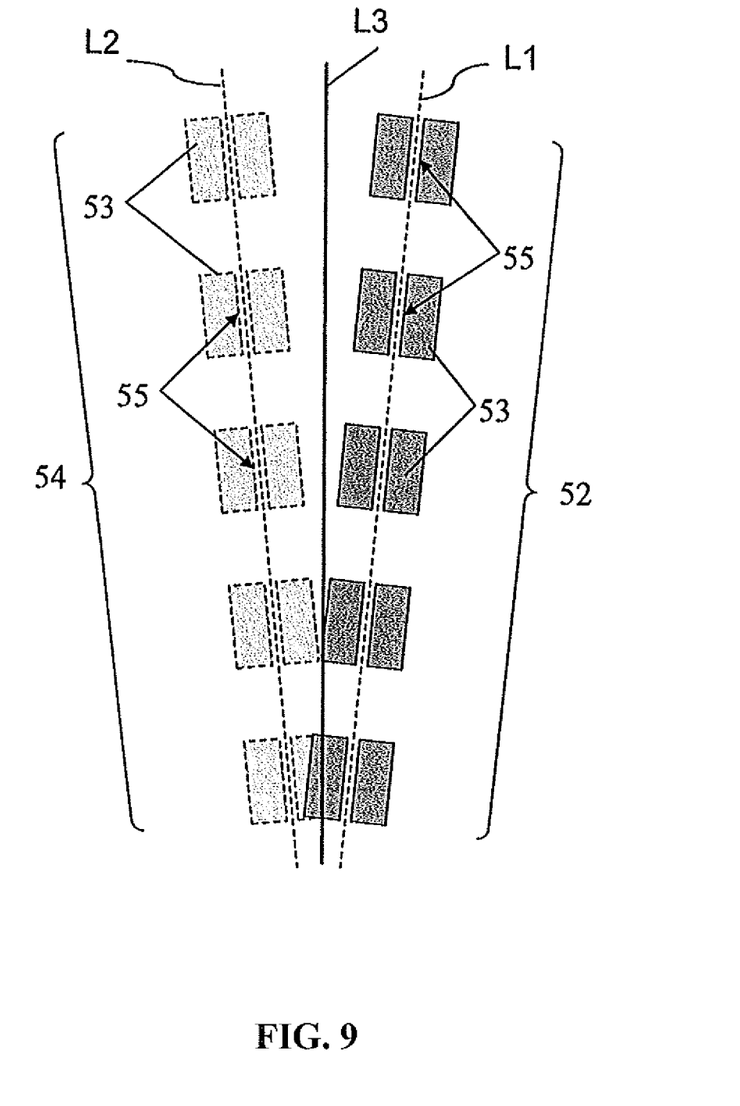
FIG. 9 is a schematic illustration of two views of the rotational axis registration plate of FIG. 8.

Next, similar to the images taken of the collimator 16, the digital camera 26 is used to acquire digital images of the two sides 52, 54 of the rotational axis registration plate 50 by photographing the first side 52 and then rotating the fixture 28 about its rotational axis A and photographing the second side 54. FIG. 9 shows the two images, one of the first side 52 and the other of the second side 54 overlaid. In each of the images, the processor 46 performs an appropriate image processing algorithm to fit a best-fit straight line through the plurality of slits 55. The line L1 represents the best-fit line determined for the image of the first side 52. The line L2 represents the best-fit line determined for the image of the second side 54. The image processor 46 then determines a bisector L3 of the lines L1 and L2. Thus, the position of the bisector L3 line in the camera's field of view represents the rotational axis A of the fixture 28. This positional information for the rotational axis A is then utilized for the flipping of one of the two image data of the collimator 16 discussed above. Determining the exact location of the rotational axis A this way corrects any rotational error introduced by the fact that the rotational axis A and the center of the collimator 16 may not be perfectly aligned. By flipping one of the two image data of the collimator 16 about the rotational axis A represented by the bisector L3, the two image data can be properly compared for determining the relative positions of the channel openings without the rotational error attributable to the rotational axis A.

In addition to the rotational error, another source for distortion of the images taken by the camera 26 is an intrinsic distortions that can result from the aberrations of the camera's optics and the camera's optical axis may not be perfectly perpendicular to the y-axis. Hence, this may result in a small component of "trapezoid" distortion, where the local magnification in the image varies slightly from top to bottom. This trapezoid distortion must also be corrected. This composite system distortion, due to the intrinsic component from camera 26 optics and the trapezoid component due to residual misalignment in the system 24, can be corrected or compensated for by using a calibration plate 36. The calibration plate 36 is shown in FIGS. 10A and 10B.

Figure 10A:
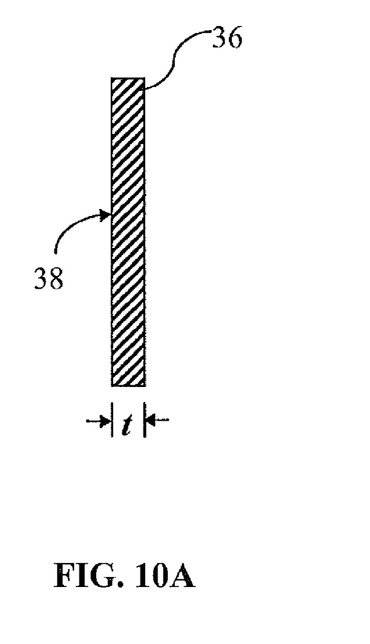
FIGS. 10A and 10B are a side view and a plan view of a calibration plate used in the method of the present disclosure.
Figure 10B:
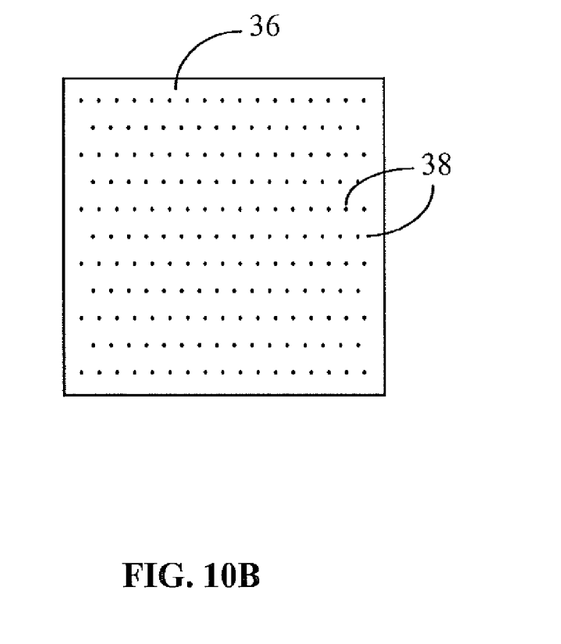

FIG. 10A shows a side view of the calibration plate 36 and FIG. 10B shows a plan view of the calibration plate 36. The calibration plate 36 is intended to be mounted in the same fixture 28 used for imaging the collimator 16. The calibration plate 36 has the same thickness t as the collimator 16 so that when the calibration plate is mounted in the fixture 28 the surface of the calibration plate facing the camera 26 is at the distance D from the camera 26, same as the collimator 16. The calibration plate 26 is provided with a precision pattern of calibration dots 38 that substantially fill the field-of-view of the camera 26. In the illustrated example, the precision pattern of calibration dots 38 is a 2-dimensional array of dots whose precise spatial positions are known. As discussed above in connection with locating the position of the rotational axis A, the precise positions of the calibration dots 38 are known to ±10 μm.

By acquiring a digital image of the calibration dots 38 on the calibration plate 36, one can determine the combined distortion characteristic of the camera 26 and the photographic fixture, FIG. 5, by processing the digital image data and determining the spatial positional deviation of the calibration dots 38 in the digital image from their true positions. The spatial deviation of the calibration dots 38 measured in the digital image of the calibration plate 36 is then used to correct the spatial distortions in the digital images of the collimator 16 taken by the camera 26, attributable to the intrinsic distortion of the camera 26 and the trapezoidal distortion due to the residual non-perpendicularity of the optical axis O with rotation axis A. It will be appreciated that the precision pattern provided on the calibration plate 36 can be a pattern comprised of geometric shapes other than dots. In one embodiment, the calibration plate 36 may be rectangular and slightly larger than the collimator itself, but it has the same thickness t as the collimator 16 being characterized. This process of correcting the intrinsic distortion of the camera 26 will be referred to herein as calibrating the camera.

It will be appreciated that the calibration of the camera 26 only needs to be performed once for that particular camera hardware and the mechanical set up. Mechanical set up refers to the spatial relationship between the camera 26 and the fixture 28. This is because, if the mechanical set up changes, the relative positions of the camera 26 and the fixture 28 will change and, in turn, the position of the image subject (i.e., the collimator 16 or the calibration plate 36) within the camera's field-of-view will change. If the camera hardware is replaced or the mechanical set up is changed, a new calibration data should be generated. The calibration data can be stored in the system controller's 44 data storage unit 48 and image processing of any images acquired by the camera 26 would apply the correction to the image data.

Additionally, the calibration of the camera 26 can be performed before or after the digital images of the collimator 16 are acquired for generating the vector map. The calibration data for the camera just need to be available in order to conduct the image processing to generate the vector map from the first and second image data of the collimator 16.

In another embodiment, the characterization system 24 can employ two digital cameras. The two cameras would be positioned facing each other with the fixture 28 positioned in the middle. Then, images of the two sides of the collimator 16 can be taken without rotating the collimator 16. This would eliminate the need for correcting the rotational error of the fixture 28. However, the positions of the two cameras becomes critical so that the two images of the collimator 16 taken by the two cameras can register perfectly when overlapped. However, because there are two cameras, each camera must be calibrated individually to correct for their intrinsic distortion and the residual misalignment of their respective optical axes. In this embodiment, the calibration plate 36 would be double sided and the precision calibration dot pattern 38 would be provided on both sides of the calibration plate 36. Each of the two cameras would image the corresponding sides of both the calibration plate 36 and the collimator 16. As in the previous embodiment, the calibration plate 36 would have the same thickness t as the collimator 16 so that the distance between the camera and the features being photographed (the collimator holes 20 and the calibration patterns) does not change.

In this embodiment, registration (i.e. alignment) of the first and second side images can be provided by positioning a pair of registration features (one on left side and one on the right side) in the calibration plate 36 viewable from both the first and second sides. Such registration features could be a pair of holes or a pair of pins that extend through the thickness of the calibration plate 36. Since there is a discrete set of holes or pins (at least two) viewable from both sides of the calibration plate 16 that can be identified and localized on the image of each side, the coordinates for the front and back images can be correlated. In other words, because the center offset and the rotation offset (the mechanical offsets) are known, and hence the positions determined in the images can be given in a common coordinate set.

In both embodiments (one camera vs. two cameras), the first and second images of the collimator 16 need to be distortion corrected and represented in a common coordinate system. This in turn allows the x, y-differences or translations between the two channel openings of the collimator channels to be determined, and thereby the orientation vectors of the collimator channels can be determined.

The first and second image data generated by the characterization system 24 represent two-dimensional digital images of each side 34, 42 of the collimator 16. The two image data are subjected to one or more computer processing steps to relate the imaged positions of the channel openings on the first side 34 of the collimator to the imaged positions of the channel openings on the second side 42.

The processor 46 may execute instructions for collecting and analyzing the collimator digital image data obtained by the camera 26 (or cameras, where the two-camera embodiment is used).

Figure 11:
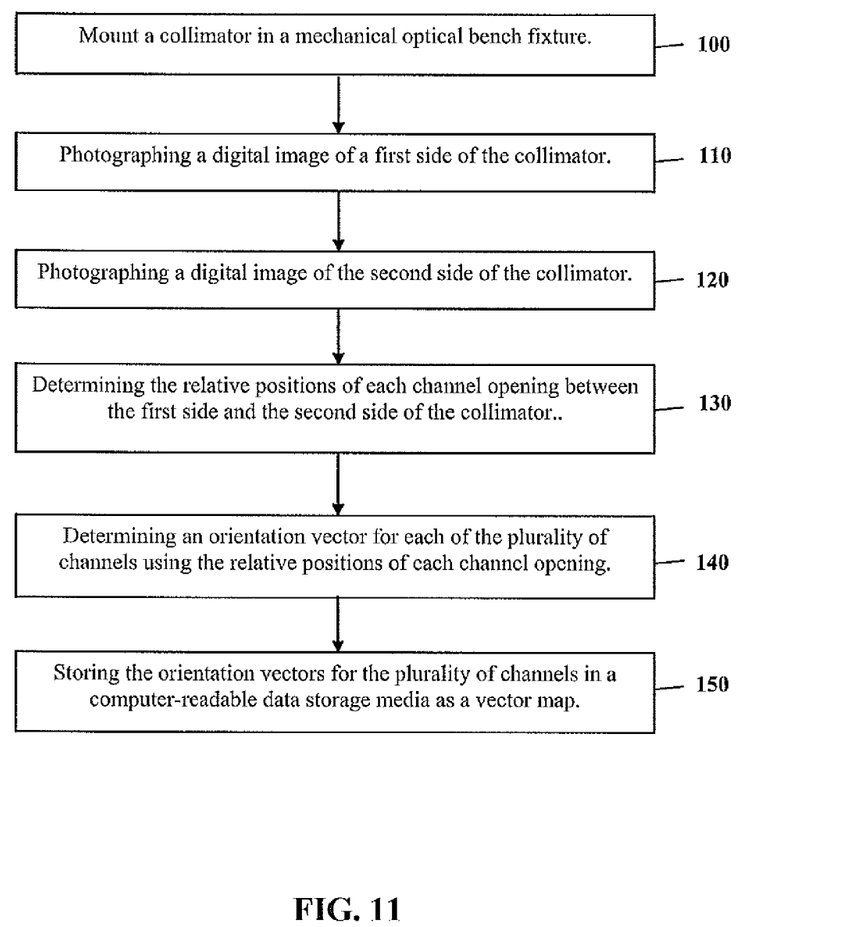
FIG. 11 is a flowchart detailing and embodiment of the method of the present disclosure.

Referring now to FIG. 11, a method of obtaining a vector map of a collimator according to one embodiment will be described. At step 100, the collimator 16 is mounted in a mechanical optical bench fixture 28 in the calibration system 24. At step 110, a digital image of the first side 34 of the collimator 16 is photographed using the camera 26 and obtaining a first image data representing the positions of each channel opening on the first side of the collimator. At step 120, a digital image of the second side 42 of the collimator 16 is photographed using the camera 26 and obtaining a second image data representing the positions of each channel opening on the second side of the collimator. At step 130, the relative positions of each channel opening between the first side and the second side of the collimator is determined by correlating the first image data to the second image data. At step 140, an orientation vector is determined for each of the plurality of channels using the relative positions. At step 150, the orientation vectors for the plurality of channels are stored in a computer-readable data storage media as a vector map comprising an array of the orientation vectors. The vector map can be stored in a data storage media as a firmware associated with the collimator 16.

The method described herein may be automated by, for example, tangibly embodying a program of instructions upon a computer readable storage media capable of being read by machine capable of executing the instructions. A general purpose computer is one example of such a machine. A non-limiting exemplary list of appropriate storage media well known in the art would include such devices as a readable or writeable CD, DVD, flash memory chips (e.g., thumb drives), various magnetic storage media, and the like.

The features of the system and method have been disclosed, and further variations will be apparent to persons skilled in the art. Such variations are considered to be within the scope of the appended claims. Reference should be made to the appended claims, rather than the foregoing specification, as indicating the true scope of the disclosed system and method.

The functions and process steps herein may be performed automatically or wholly or partially in response to user command. An activity (including a step) performed automatically is performed in response to executable instruction or device operation without user direct initiation of the activity.

The systems and processes disclosed herein are not exclusive. Other systems, processes and menus may be derived in accordance with the principles of the invention to accomplish the same objectives. Although this invention has been described with reference to particular embodiments, it is to be understood that the embodiments and variations shown and described herein are for illustration purposes only. Modifications to the current design may be implemented by those skilled in the art, without departing from the scope of the invention. The processes and applications may, in alternative embodiments, be located on one or more (e.g., distributed) processing devices accessing a network linking the elements of FIG. 1. Further, the functions and steps of the disclosed method may be implemented in hardware, software or a combination of both and may reside on one or more processing devices located at a location of a network linking the elements of FIG. 1 or another linked network, including the Internet.

What is claimed is:

1. A method for obtaining a channel orientation vector map of a multi-channel collimator for a nuclear medicine imaging system to correct for angular pointing errors in channels of said multi-channel collimator, said multi-channel collimator having a first side and a second side and a plurality of channels extending there through, each of the plurality of channels forming openings at the first side and the second side of the collimator, said method comprising:

photographing a digital image of the first side of the collimator and obtaining first image data representing the positions of each channel opening on the first side of the collimator;

photographing a digital image of the second side of the collimator and obtaining second image data representing the positions of each channel opening on the second side of the collimator;

determining the relative positions of each channel opening between the first side and the second side of the collimator by correlating the first image data to the second image data;

determining an orientation vector for each of the plurality of channels using said relative positions; and     generating a channel orientation vector map of said orientation vectors for use in image reconstruction in said nuclear medicine imaging system.

2. The method of claim 1, wherein photographing the digital images are performed using a digital camera.

3. The method of claim 2, further comprising calibrating the digital camera using a calibration plate having a pattern of calibration dots to generate camera calibration data and correcting for any intrinsic distortion of the camera by applying the calibration data to the first and second image data before determining the relative positions of each channel opening between the first side and the second side of the collimator by comparing the first image data to the second image data.

4. The method of claim 1, wherein determining the orientation vector for each of the plurality of channels using said relative positions comprises determining angular deviations of the channel in x-axis direction and y-axis direction.

5. The method of claim 1, further comprising storing said channel orientation vector map in a memory associated with the collimator.

6. The method of claim 1, wherein the collimator is mounted on a rotatable fixture rotatable about its rotational axis and the digital images of the first and second sides of the collimator are photographed using a digital camera, and the method further comprising rotating the collimator 180 degrees in order to photograph the second side of the collimator and the method further comprising correcting for a rotational error of the rotatable fixture.

7. The method of claim 6, wherein correcting for the rotational error of the rotatable fixture comprises mounting a rotational axis registration plate on the rotatable fixture in lieu of the collimator, wherein the rotational axis registration plate has a first side and a second side and one or more slits that are longitudinally oriented along the rotational axis of the rotatable fixture and are visible from each of the two sides; and
  photographing the first side of the rotational axis registration plate and obtaining a first image data of the one or more slits;
  rotating the rotational axis registration plate 180 degrees;
  photographing the second side of the rotational axis registration plate and obtaining a second image data of the one or more slits; and
  determining the location of the rotational axis of the rotatable fixture by comparing the first image data of the one or more slits against the second image data of the one or more slits.

8. The method of claim 7, wherein determining the location of the rotational axis comprises:
  best-fitting a line through the one or more slits in the first image data of the one or more slits;
  best-fitting a line through the one or more slits in the second image data of the one or more slits; and
  determining a bisector of the two lines which represents the rotational axis.

9. The method of claim 1, wherein the step of photographing the first side of the collimator is performed with a first camera and the step of photographing the second side of the collimator is performed with a second camera, wherein the collimator is positioned in between the two cameras and the collimator is not rotated between photographing the first side and photographing the second side.

10. A system for obtaining collimator channel vectors to correct for angular pointing errors in channels of a multi-channel collimator of a nuclear medicine imaging system, comprising:
  a digital camera;
  a processor; and
  a memory storing processor executable instructions for obtaining a channel orientation vector map of said multi-channel collimator, said multi-channel collimator having a first side and a second side and a plurality of channels extending there through, each of the plurality of channels forming openings at the first side and the second side of the collimator, said instructions comprising instructions causing the processor to:
  obtain a digital image of the first side of the collimator using the digital camera and obtaining a first image data representing the positions of each channel openings on the first side of the collimator;
  obtain a digital image of the second side of the collimator using the digital camera and obtaining second image data representing the positions of the channel openings on the second side of the collimator;
  determine the relative positions of each channel opening between the first side and the second side of the collimator by correlating the first image data to the second image data;
  determine an orientation vector for each of the plurality of channels using said relative positions; and
  generate a channel orientation vector map of said orientation vectors for use in image reconstruction in said nuclear medicine imaging system.

11. The system of claim 10, wherein the digital images are obtained using a digital camera.

12. The system of claim 11, wherein the instructions further comprise instructions causing the processor to calibrate the digital camera using a calibration plate having a pattern of calibration dots to generate a camera calibration data and correcting for any intrinsic distortion of the camera by applying the calibration data to the first and second image data before determining the relative positions of each channel opening between the first side and the second side of the collimator by comparing the first image data to the second image data.

13. The system of claim 10, determining the orientation vector for each of the plurality of channels using said relative positions include determining angular deviations of the channel in x-axis direction and y-axis direction.

14. The system of claim 10, wherein the instructions further comprise instructions causing the processor to store said orientation vectors for each of the plurality of channels in a memory associated with the collimator as an array forming said vector map.

15. The system of claim 10, further comprising a rotatable fixture rotatable about its rotational axis, said collimator being mountable on said rotatable fixture and the digital images of the first and second sides of the collimator being photographed using a digital camera, the collimator being rotated 180 degrees in order to photograph the second side of the collimator; the instructions further comprising instructions causing the processor to correct for a rotational error of the rotatable fixture.

16. The system of claim 15, wherein correcting for the rotational error of the rotatable fixture comprises mounting a rotational axis registration plate on the rotatable fixture in lieu of the collimator, wherein the rotational axis registration plate has a first side and a second side and one or more slits that are longitudinally oriented along the rotational axis of the rotatable fixture and are visible from each of the two sides; and
  photographing the first side of the rotational axis registration plate and obtaining a first image data of the one or more slits;
  rotating the rotational axis registration plate 180 degrees;

photographing the second side of the rotational axis registration plate and obtaining a second image data of the one or more slits; and determining the location of the rotational axis of the rotatable fixture by comparing the first image data of the one or more slits against the second image data of the one or more slits.

17. The system of claim 16, wherein determining the location of the rotational axis comprises:

best-fitting a line through the one or more slits in the first image data of the one or more slits;

best-fitting a line through the one or more slits in the second image data of the one or more slits; and determining a bisector of the two lines which represents the rotational axis.

18. The system of claim 16, wherein photographing the first side of the collimator is performed with a first camera and photographing the second side of the collimator is performed with a second camera, wherein the collimator is positioned in between the two cameras and the collimator is not rotated between photographing the first side and photographing the second side.

* * * * *